US010350395B2

(12) United States Patent
Roeder

(10) Patent No.: US 10,350,395 B2
(45) Date of Patent: Jul. 16, 2019

(54) INTRODUCER FOR LUMEN SUPPORT OR DILATION

(71) Applicant: COOK MEDICAL TECHNOLOGIES LLC, Bloomington, IN (US)

(72) Inventor: Blayne A. Roeder, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 82 days.

(21) Appl. No.: 15/631,759

(22) Filed: Jun. 23, 2017

(65) Prior Publication Data

US 2018/0369544 A1  Dec. 27, 2018

(51) Int. Cl.
*A61M 25/10* (2013.01)
*A61F 2/04* (2013.01)
(Continued)

(52) U.S. Cl.
CPC ............. *A61M 25/104* (2013.01); *A61F 2/04* (2013.01); *A61M 25/1011* (2013.01);
(Continued)

(58) Field of Classification Search
CPC .. A61M 25/104; A61M 25/1011–1015; A61M 2025/1045; A61M 2025/1043;
(Continued)

(56) References Cited

U.S. PATENT DOCUMENTS 4,338,942 A  7/1982 Fogarty
4,403,612 A  9/1983 Fogarty
(Continued)

FOREIGN PATENT DOCUMENTS

DE  20 2011 003097 U1  7/2011
EP  2672925 A2  12/2013
(Continued)

OTHER PUBLICATIONS

Extended European Search Report for EP Application No. 18275082, dated Nov. 22, 2018, 11 pages.
(Continued)

*Primary Examiner* — Shaun David
*Assistant Examiner* — Brigid K Byrd
(74) *Attorney, Agent, or Firm* — Brinks Gilson & Lione

(57) ABSTRACT

A system for supporting or dilating a body vessel includes a balloon catheter with a shaft having a delivery lumen in communication with an interior of the balloon. The balloon includes holes formed in the outer wall of the balloon. Additional or daughter balloons are delivered through the delivery lumen into the cavity of the balloon and through the holes into engagement with the holes. The daughter balloons are inflatable to seal against the holes, and the main balloon is subsequently inflatable when sealed by the daughter balloons. The daughter balloons may be delivered to branch vessels to provide support in addition to the inflation of the main balloon. The system may include preloaded wires extending through the delivery lumen and through the holes, and the daughter balloons can be delivered over the wires to the desired location.

16 Claims, 4 Drawing Sheets

(51) Int. Cl.
  *A61M 29/02* (2006.01)
  *A61M 25/00* (2006.01)
  *A61F 2/954* (2013.01)
  *A61F 2/958* (2013.01)

(52) U.S. Cl.
  CPC ......... *A61M 25/1034* (2013.01); *A61F 2/954* (2013.01); *A61F 2/958* (2013.01); *A61M 29/02* (2013.01); *A61M 2025/0063* (2013.01); *A61M 2025/1045* (2013.01); *A61M 2025/1081* (2013.01); *A61M 2025/1095* (2013.01)

(58) Field of Classification Search
  CPC ... A61M 2025/1072; A61M 2025/1081; A61F 2/95; A61F 2/954; A61F 2/958; A61F 2002/821; A61B 17/12136
  See application file for complete search history.

(56) References Cited

U.S. PATENT DOCUMENTS

| | | | |
|---|---|---|---|
| 4,744,366 A | 5/1988 | Jang | |
| 4,748,982 A * | 6/1988 | Horzewski | A61M 25/0054 604/102.02 |
| 5,049,132 A | 9/1991 | Shaffer et al. | |
| 5,061,273 A * | 10/1991 | Yock | A61B 18/245 604/103.04 |
| 5,163,905 A * | 11/1992 | Don Michael | A61M 25/1011 604/101.03 |
| 5,318,531 A | 6/1994 | Leone | |
| 5,342,301 A | 8/1994 | Saab | |
| 5,366,472 A | 11/1994 | Hillstead | |
| 5,405,472 A | 4/1995 | Leone | |
| 5,447,497 A | 9/1995 | Sogard et al. | |
| 5,470,313 A | 11/1995 | Crocker et al. | |
| 5,505,700 A * | 4/1996 | Leone | A61F 2/958 604/101.03 |
| 5,558,642 A * | 9/1996 | Schweich, Jr. | A61M 25/1002 604/101.05 |
| 5,562,620 A * | 10/1996 | Klein | A61M 25/104 604/101.05 |
| 5,569,184 A * | 10/1996 | Crocker | A61F 2/88 604/103.01 |
| 5,569,195 A | 10/1996 | Saab | |
| 5,576,476 A | 11/1996 | Moots | |
| 5,617,878 A * | 4/1997 | Taheri | A61B 8/12 128/898 |
| 5,628,730 A | 5/1997 | Shapland et al. | |
| 5,645,560 A | 7/1997 | Crocker et al. | |
| 5,676,697 A * | 10/1997 | McDonald | A61F 2/07 623/1.35 |
| 5,707,358 A * | 1/1998 | Wright | A61M 25/1011 604/103.07 |
| 5,725,535 A | 3/1998 | Hegde et al. | |
| 5,755,734 A * | 5/1998 | Richter | A61F 2/07 128/898 |
| 5,788,708 A | 8/1998 | Hegde et al. | |
| 5,792,105 A | 8/1998 | Lin et al. | |
| 5,797,948 A | 8/1998 | Dunham | |
| 5,810,767 A * | 9/1998 | Klein | A61B 8/12 604/103.01 |
| 5,823,996 A | 10/1998 | Sparks | |
| 5,833,567 A | 11/1998 | Reinhardt et al. | |
| 5,833,659 A | 11/1998 | Kranys | |
| 5,843,027 A * | 12/1998 | Stone | A61F 2/958 604/509 |
| 5,843,033 A * | 12/1998 | Ropiak | A61M 25/104 604/103.01 |
| 5,843,116 A | 12/1998 | Crocker et al. | |
| 5,860,954 A | 1/1999 | Ropiak | |
| 5,924,973 A | 7/1999 | Weinberger | |
| 6,007,517 A * | 12/1999 | Anderson | A61M 25/104 604/103.04 |
| 6,017,363 A * | 1/2000 | Hojeibane | A61F 2/856 606/194 |
| 6,027,517 A | 2/2000 | Crocker et al. | |
| 6,059,824 A * | 5/2000 | Taheri | A61F 2/856 623/1.15 |
| 6,096,073 A * | 8/2000 | Webster | A61F 2/91 623/1.16 |
| 6,120,523 A | 9/2000 | Crocker et al. | |
| 6,123,712 A | 9/2000 | Di Caprio et al. | |
| 6,156,053 A | 12/2000 | Gandhi et al. | |
| 6,159,227 A | 12/2000 | Di Caprio et al. | |
| 6,196,230 B1 * | 3/2001 | Hall | A61F 2/2493 128/898 |
| 6,210,429 B1 * | 4/2001 | Vardi | A61F 2/856 606/153 |
| 6,290,673 B1 * | 9/2001 | Shanley | A61F 2/954 604/102.02 |
| 6,325,814 B1 | 12/2001 | Euteneuer et al. | |
| 6,325,826 B1 * | 12/2001 | Vardi | A61F 2/82 623/1.15 |
| 6,330,884 B1 * | 12/2001 | Kim | A61B 17/11 128/898 |
| 6,409,741 B1 | 6/2002 | Crocker et al. | |
| 6,419,685 B2 | 7/2002 | Di Caprio et al. | |
| 6,428,567 B2 * | 8/2002 | Wilson | A61F 2/856 623/1.11 |
| 6,508,836 B2 | 1/2003 | Wilson et al. | |
| 6,517,533 B1 | 2/2003 | Swaminathan | |
| 6,520,988 B1 * | 2/2003 | Colombo | A61F 2/856 623/1.11 |
| 6,569,190 B2 | 5/2003 | Whalen, II et al. | |
| 6,575,966 B2 | 6/2003 | Lane et al. | |
| 6,605,030 B2 | 8/2003 | Weinberger | |
| 6,605,056 B2 | 8/2003 | Eidenschink et al. | |
| 6,632,196 B1 | 10/2003 | Houser | |
| 6,652,441 B2 | 11/2003 | Weinberger et al. | |
| 6,682,545 B1 | 1/2004 | Kester | |
| 6,719,720 B1 | 4/2004 | Voelker et al. | |
| 6,835,203 B1 * | 12/2004 | Vardi | A61F 2/82 623/1.34 |
| 6,858,038 B2 * | 2/2005 | Heuser | A61F 2/07 623/1.11 |
| 6,875,220 B2 | 4/2005 | Wilson et al. | |
| 6,896,699 B2 | 5/2005 | Wilson et al. | |
| 6,955,688 B2 | 10/2005 | Wilson et al. | |
| 7,066,905 B2 | 6/2006 | Squire et al. | |
| 7,083,643 B2 | 8/2006 | Whalen, II et al. | |
| 7,300,433 B2 | 11/2007 | Lane et al. | |
| 7,344,557 B2 * | 3/2008 | Yadin | A61F 2/82 604/103.06 |
| 7,384,411 B1 * | 6/2008 | Condado | A61M 25/0075 604/101.01 |
| 7,438,722 B1 | 10/2008 | Hassainy | |
| 7,524,321 B2 | 4/2009 | Saab | |
| 7,527,622 B2 | 5/2009 | Lane et al. | |
| 7,553,324 B2 | 6/2009 | Andreas et al. | |
| 7,648,497 B2 | 1/2010 | Lane et al. | |
| 7,670,364 B2 | 3/2010 | Dusbabek et al. | |
| 7,708,772 B2 | 5/2010 | Wilson et al. | |
| 7,753,950 B2 | 7/2010 | Wislon et al. | |
| 7,771,462 B1 * | 8/2010 | Davidson | A61F 2/954 623/1.11 |
| 7,799,064 B2 * | 9/2010 | Brucker | A61F 2/954 623/1.11 |
| 7,871,431 B2 | 1/2011 | Gurm et al. | |
| 7,942,847 B2 | 5/2011 | Stupecky et al. | |
| 7,955,253 B2 | 6/2011 | Ewers et al. | |
| 8,034,022 B2 | 10/2011 | Boatman | |
| 8,109,904 B2 | 2/2012 | Papp | |
| 8,162,879 B2 | 4/2012 | Hattangadi et al. | |
| 8,182,446 B2 | 5/2012 | Schaeffer et al. | |
| 8,211,055 B2 | 7/2012 | Christiansen | |
| 8,298,217 B2 | 10/2012 | Lane et al. | |
| 8,317,747 B2 | 11/2012 | Kusleika | |
| 8,333,757 B2 | 12/2012 | Mazzone et al. | |
| 8,357,118 B2 | 1/2013 | Orr | |
| 8,377,108 B2 * | 2/2013 | Jennings | A61F 2/856 623/1.11 |
| 8,540,758 B2 * | 9/2013 | Nanavati | A61F 2/856 623/1.11 |

(56) References Cited

U.S. PATENT DOCUMENTS

| | | | |
|---|---|---|---|
| 8,568,648 B2 | 10/2013 | Stupecky et al. | |
| 8,591,461 B2 | 11/2013 | Boatman | |
| 8,603,030 B2 | 12/2013 | Papp | |
| 8,668,667 B2 | 3/2014 | Chappa | |
| 8,672,919 B2 | 3/2014 | Shirley et al. | |
| 8,690,822 B2 | 4/2014 | Papp | |
| 8,696,644 B2 | 4/2014 | Baumbach et al. | |
| 8,715,230 B2 | 5/2014 | Baumbach et al. | |
| 8,734,501 B2 | 5/2014 | Hartley et al. | |
| 8,740,843 B2 | 6/2014 | Eaton et al. | |
| 8,769,796 B2 * | 7/2014 | Bourang | A61L 31/16 29/508 |
| 8,784,602 B2 | 7/2014 | Schaeffer et al. | |
| 8,795,227 B2 | 8/2014 | Condado | |
| 8,795,347 B2 | 8/2014 | Bourang et al. | |
| 8,808,236 B2 | 8/2014 | Orr | |
| 8,808,347 B2 | 8/2014 | Bourang et al. | |
| 8,814,826 B2 | 8/2014 | Foreman et al. | |
| 8,821,562 B2 | 9/2014 | Bourang et al. | |
| 8,827,953 B2 | 9/2014 | Rocha-Singh | |
| 8,828,071 B2 | 9/2014 | Bourang et al. | |
| 8,979,917 B2 | 3/2015 | Bourang et al. | |
| 9,028,443 B2 | 5/2015 | McCullough | |
| 9,034,025 B2 | 5/2015 | Sanati et al. | |
| 9,119,716 B2 | 9/2015 | Lee et al. | |
| 9,119,944 B2 | 9/2015 | Chambers et al. | |
| 9,174,030 B2 | 11/2015 | Boatman | |
| 9,186,486 B2 | 11/2015 | Weber et al. | |
| 9,205,233 B2 | 12/2015 | Gulcher | |
| 9,339,384 B2 | 5/2016 | Tan et al. | |
| 9,364,356 B2 | 6/2016 | Bourang | |
| 9,370,644 B2 | 6/2016 | Rocha-singh | |
| 9,375,223 B2 | 6/2016 | Wallace | |
| 9,480,826 B2 | 11/2016 | Schneider et al. | |
| 9,486,342 B2 * | 11/2016 | Al-Saadon | A61F 2/856 |
| 9,486,347 B2 * | 11/2016 | Chuter | A61F 2/958 |
| 9,526,506 B2 | 12/2016 | Shibata et al. | |
| 9,550,046 B1 | 1/2017 | Allen et al. | |
| 9,649,478 B2 | 5/2017 | Baumbach et al. | |
| 9,649,479 B2 | 5/2017 | Baumbach et al. | |
| 9,707,078 B2 | 7/2017 | Madrid et al. | |
| 9,724,218 B2 | 8/2017 | Bourang et al. | |
| 9,724,495 B2 | 8/2017 | McCullough | |
| 9,730,726 B2 * | 8/2017 | Bacino | A61B 17/320725 |
| 9,730,821 B2 | 8/2017 | Bourang et al. | |
| 9,737,424 B2 | 8/2017 | Bourang et al. | |
| 9,743,973 B2 | 8/2017 | Pageard | |
| 9,833,600 B2 | 12/2017 | Stupecky et al. | |
| 9,855,258 B1 | 1/2018 | Bourang et al. | |
| 9,888,927 B2 | 2/2018 | Belfort et al. | |
| 9,937,255 B2 | 4/2018 | Ogle et al. | |
| 9,943,422 B2 | 4/2018 | Hartley et al. | |
| 2001/0016766 A1 * | 8/2001 | Vardi | A61F 2/82 623/1.11 |
| 2002/0077651 A1 * | 6/2002 | Holmes, Jr. | A61M 29/02 606/190 |
| 2002/0143383 A1 * | 10/2002 | Parodi | A61F 2/954 623/1.11 |
| 2002/0156518 A1 * | 10/2002 | Tehrani | A61F 2/07 623/1.11 |
| 2003/0028233 A1 * | 2/2003 | Vardi | A61F 2/954 623/1.11 |
| 2003/0036728 A1 * | 2/2003 | Samson | A61B 17/12045 604/103.01 |
| 2003/0097169 A1 * | 5/2003 | Brucker | A61F 2/856 623/1.11 |
| 2003/0120208 A1 * | 6/2003 | Houser | A61F 2/95 604/103.04 |
| 2003/0135257 A1 * | 7/2003 | Taheri | A61B 17/00234 623/1.11 |
| 2004/0138737 A1 * | 7/2004 | Davidson | A61F 2/82 623/1.35 |
| 2004/0143286 A1 * | 7/2004 | Johnson | A61F 2/856 606/194 |
| 2005/0010277 A1 * | 1/2005 | Chuter | A61F 2/064 623/1.13 |
| 2005/0154442 A1 * | 7/2005 | Eidenschink | A61F 2/856 623/1.11 |
| 2005/0192656 A1 * | 9/2005 | Eidenschink | A61F 2/07 623/1.11 |
| 2005/0245941 A1 * | 11/2005 | Vardi | A61F 2/954 606/108 |
| 2006/0100694 A1 * | 5/2006 | Globerman | A61F 2/856 623/1.35 |
| 2006/0265041 A1 | 11/2006 | Sanati et al. | |
| 2006/0265043 A1 * | 11/2006 | Mandrusov | A61B 5/02007 623/1.11 |
| 2006/0271093 A1 * | 11/2006 | Holman | A61F 2/958 606/194 |
| 2007/0016241 A1 * | 1/2007 | von Oepen | A61F 2/958 606/192 |
| 2007/0208256 A1 * | 9/2007 | Marilla | A61B 5/02007 600/467 |
| 2007/0260217 A1 * | 11/2007 | Von Oepen | A61F 2/954 604/509 |
| 2007/0282419 A1 * | 12/2007 | Hilaire | A61F 2/856 623/1.11 |
| 2008/0051869 A1 * | 2/2008 | Yribarren | A61F 2/954 623/1.11 |
| 2008/0177370 A1 * | 7/2008 | Stys | A61F 2/82 623/1.15 |
| 2008/0243233 A1 * | 10/2008 | Ben-Muvhar | A61F 2/954 623/1.35 |
| 2009/0171430 A1 * | 7/2009 | Baim | A61F 2/954 623/1.11 |
| 2009/0182270 A1 * | 7/2009 | Nanavati | A61F 2/856 604/96.01 |
| 2009/0292241 A1 * | 11/2009 | von Oepen | A61F 2/958 604/96.01 |
| 2010/0222861 A1 * | 9/2010 | Dibie | A61F 2/856 623/1.11 |
| 2011/0054586 A1 * | 3/2011 | Mayberry | A61F 2/07 623/1.11 |
| 2011/0190584 A1 * | 8/2011 | Sugahara | A61B 17/0057 600/116 |
| 2011/0282195 A1 * | 11/2011 | Solar | A61M 25/0026 600/431 |
| 2011/0282274 A1 * | 11/2011 | Fulton, III | A61M 1/3403 604/28 |
| 2012/0089220 A1 * | 4/2012 | Lualdi | A61F 2/856 623/1.35 |
| 2012/0209368 A1 | 8/2012 | Oepen | |
| 2013/0046371 A1 * | 2/2013 | Greenberg | A61F 2/07 623/1.11 |
| 2013/0268047 A1 * | 10/2013 | Bourang | A61F 2/852 623/1.11 |
| 2013/0331762 A1 * | 12/2013 | Kassab | A61M 1/369 604/9 |
| 2014/0214147 A1 * | 7/2014 | Al-Saadon | A61F 2/856 623/1.11 |
| 2015/0230951 A1 * | 8/2015 | Al-Saadon | A61F 2/954 623/1.35 |
| 2016/0022411 A1 * | 1/2016 | Greenberg | A61F 2/07 623/1.11 |
| 2017/0259033 A1 * | 9/2017 | Erickson | A61F 2/958 |
| 2017/0319359 A1 * | 11/2017 | Mehta | A61F 2/07 |

FOREIGN PATENT DOCUMENTS

| | | |
|---|---|---|
| WO | WO 98/50101 A1 | 11/1998 |
| WO | WO 00/12169 A1 | 3/2000 |
| WO | WO 2013/026135 A1 | 2/2013 |
| WO | WO 2014/029002 A1 | 2/2014 |

OTHER PUBLICATIONS

Extended European Search Report for EP Application No. 18275083, dated Nov. 7, 2018, 6 pages.

(56) References Cited

OTHER PUBLICATIONS

Extended European Search Report for EP Application No. 18275086, dated Nov. 30, 2018, 9 pages.
Extended European Search Report for EP Application No. 18275087, dated Nov. 27, 2018, 9 pages.

* cited by examiner

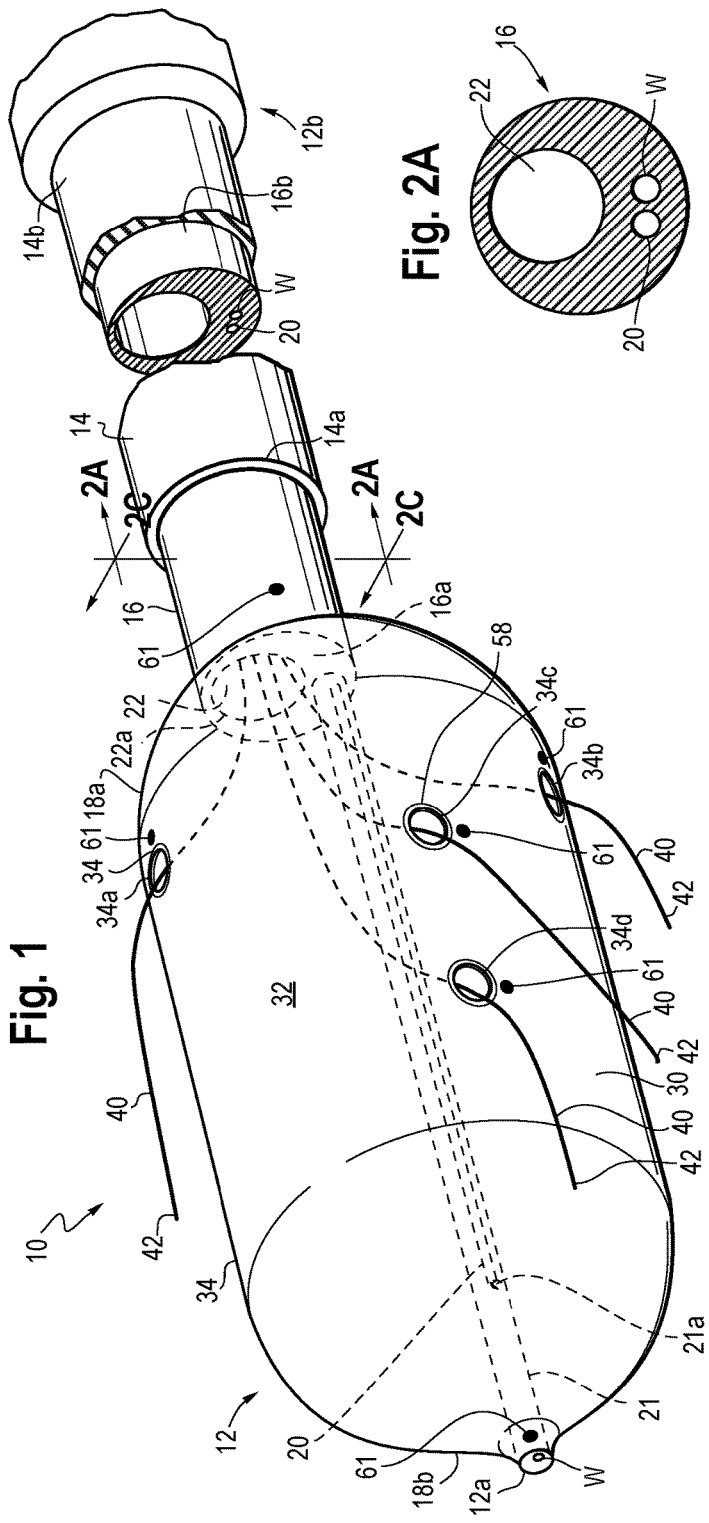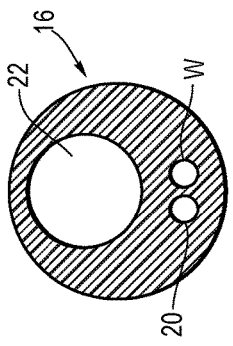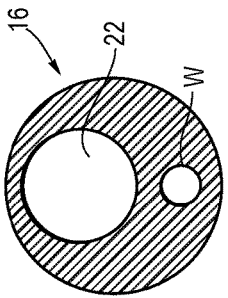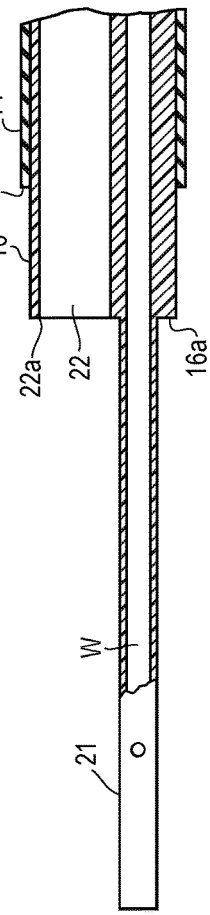

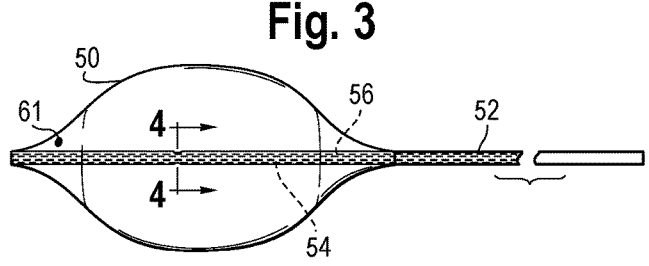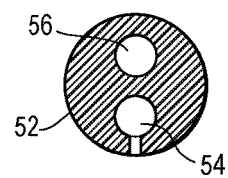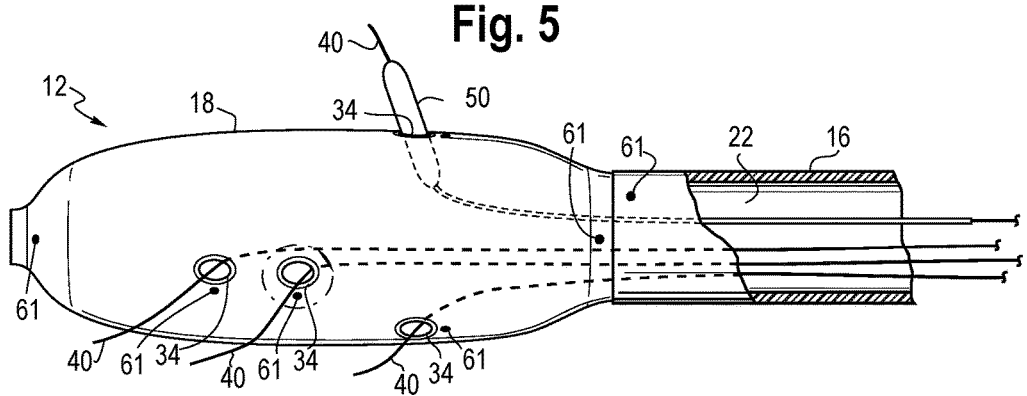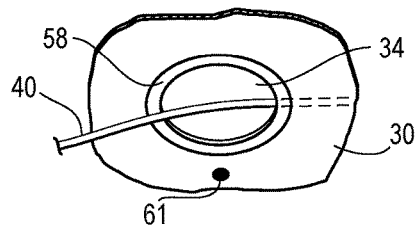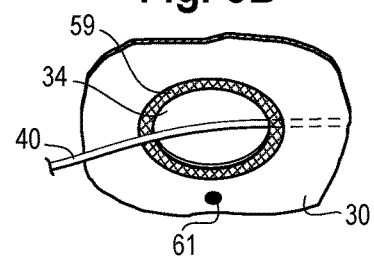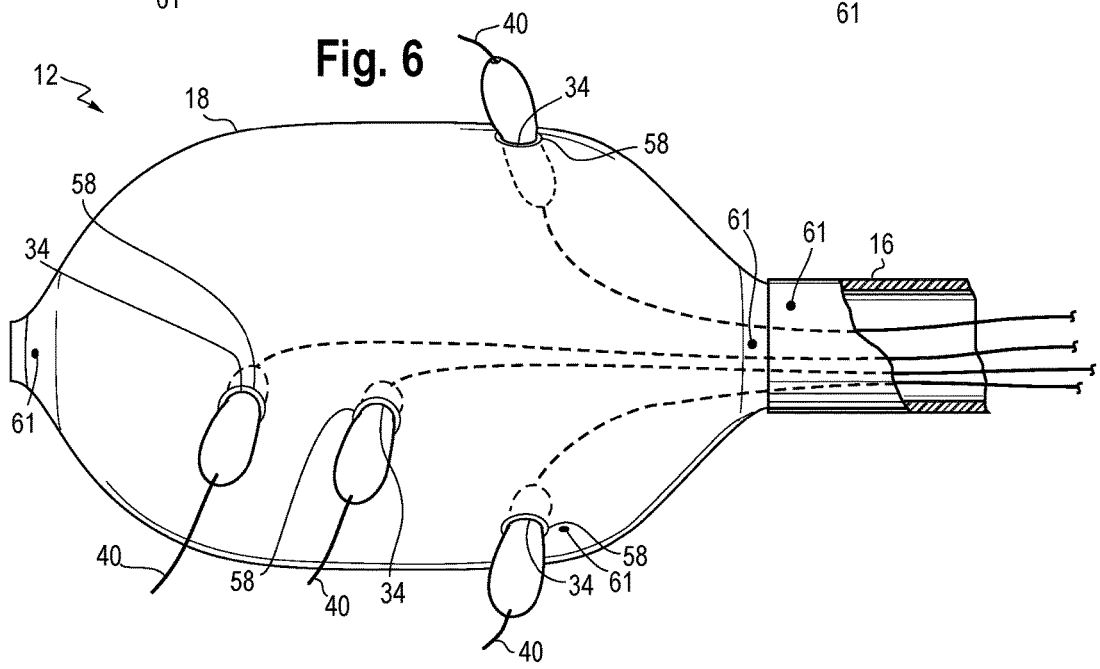

INTRODUCER FOR LUMEN SUPPORT OR DILATION

TECHNICAL FIELD

This invention relates to endoluminal medical devices for introduction into the human or animal body for treatment of endovascular disease.

BACKGROUND OF THE INVENTION

The functional vessels of human and animal bodies, such as blood vessels and ducts, occasionally weaken or even rupture. For example, the aortic wall can weaken, resulting in an aneurysm, or it may develop a tear in one of the layers of the aortic wall resulting in an aortic dissection. One common surgical intervention for weakened, aneurysmal or ruptured passageways or ducts involves the introduction of a compliant balloon into the damaged blood vessel.

One type of surgical intervention utilizing the insertion of a balloon into the patient's vasculature is Percutaneous Transluminal Angioplasty (PTA), often referred to simply as angioplasty, for opening up a blocked blood vessel. This procedures involves the insertion of a balloon catheter through the vasculature and to the desired location of the blockage. The balloon is inflated and deflated at the location of the blockage, thereby opening up the blood vessel.

Another type of surgical intervention involving balloons is a procedure where a balloon catheter is introduced toward a blood vessel, such as the aorta, to repair a dissection that has occurred. In this procedure, a compliant balloon is introduced to a location adjacent the tear in the vessel wall, and the balloon is inflated to block blood flow through the "true" lumen of the blood vessel, allowing the filling/thrombosis of the "false" lumen.

In many cases, however, the damaged or defected portion of the vasculature may include a branch vessel branching from the main vessel or may be near one of these branch vessels. For example, in the case of the abdominal aorta, there are at least four major branch vessels, including the celiac, mesenteric, and two renal arteries, as well as other vessels, leading to various other body organs.

Thus, in the case of a vessel blockage, it can be difficult to open up the blockage near the branch vessel or in the branch vessel itself with a traditional balloon, and it may be undesirable to inflate a balloon across an opening of a branch vessel to repair a blockage in a main vessel. In the case of a vessel dissection, inflating the balloon across a branch vessel opening may not effectively block the true lumen.

SUMMARY

A medical device system includes a balloon catheter having a shaft extending in a longitudinal direction and an inflatable main balloon attached to the catheter. An inflation lumen is defined by the shaft and extends longitudinally within the shaft and is in fluid communication with an interior cavity defined by the balloon for providing inflation fluid to the main balloon. A delivery lumen is defined by the shaft and extends longitudinally through the shaft. The delivery lumen is in fluid communication with the interior cavity of the balloon and is configured to allow additional medical devices to be delivered to the interior cavity of the main balloon.

The system further includes at least one inflatable daughter balloon sized and configured to be moveable through the delivery lumen and into the interior cavity of the main balloon. At least one hole is defined in an expandable wall portion of the main balloon. The hole is sized and configured to receive the daughter balloon. The daughter balloon is expandable into engagement with the at least one hole.

The main balloon may be a compliant balloon, and the daughter balloon may be a minimally compliant balloon. The hole may be pre-defined in the wall of the balloon. The balloon may be reinforced in the area around the hole.

The system may further include at least one wire extending through the delivery lumen and into the interior cavity of the main balloon from the delivery lumen. The wire may be pre-loaded in the system and may extend through the hole in the main balloon when preloaded.

The daughter balloon may include a wire lumen and may be delivered over the wire into engagement with the hole in the main balloon. The delivery lumen through which the daughter balloon is delivered may have a tubular shape and may be wider than the inflation lumen.

The daughter balloon may sealingly engage the hole when the daughter balloon is expanded such that the main balloon is inflatable after the daughter balloon is inflated. The hole may stretch in response to inflation of the daughter balloon. The daughter balloon may have an expanded width that is smaller than the expanded width of the main balloon. The daughter balloon may be expandable to a width that is greater than the hole of the main balloon.

The system may further include a tubular delivery sheath that extends over the balloon catheter in a delivery configuration, with the main balloon in a retracted position relative to an insertion end of the delivery sheath and compressed within the delivery sheath. The system has a deployed configuration where the insertion end of the delivery sheath is retracted relative to the balloon catheter to expose the balloon catheter.

In the delivery configuration, the interior cavity of the main balloon may be in fluid communication with an exterior of the main balloon via the at least one hole, and the at least one daughter balloons is not engaged with the at least one hole. In the deployed configuration, the at least one daughter balloon is engaged with the at least one hole of the main balloon and the at least one daughter balloon is inflated against the at least one hole and the interior cavity of the main balloon is sealed from the exterior of the main balloon.

The wire or wires may extend through the delivery lumen and out of the hole in the delivery configuration. The hole may be pre-defined in the wall of the balloon when balloon is in the delivery configuration. The wire or wires may alternatively extend through the delivery lumen in the delivery configuration and terminate within the interior cavity in the delivery configuration.

The daughter balloon may be outside of the delivery sheath and the balloon catheter in the delivery configuration.

In another example, a medical device system includes a balloon catheter having a shaft extending in a longitudinal direction and an inflatable main balloon attached to the catheter. The main balloon defines an interior cavity. A delivery lumen is defined by the shaft and extends longitudinally through the shaft. The delivery lumen is in fluid communication with the interior cavity of the balloon and is configured to allow additional medical devices to be delivered to the interior cavity of the main balloon.

The system further includes at least one inflatable daughter balloon sized and configured to be moveable through the delivery lumen and into the interior cavity of the main balloon.

At least one hole is defined in an expandable wall portion of the main balloon. The at least one hole is sized and configured to receive individual ones of the at least one daughter balloon. A tubular delivery sheath extends over the balloon catheter. The balloon catheter may have a delivery configuration where the balloon catheter is in a retracted position relative to an insertion end of the delivery sheath and the balloon catheter is compressed within the delivery sheath. The balloon catheter may have a deployed configuration where the insertion end of the delivery sheath is retracted relative to the balloon catheter to expose the balloon catheter.

In the delivery configuration, the interior cavity of the main balloon is in fluid communication with an exterior of the main balloon via the at least one hole, and the at least one daughter balloons is not engaged with the at least one hole.

In the deployed configuration, the at least one daughter balloon is engaged with the at least one hole of the main balloon and the at least one daughter balloon is inflated against the at least one hole, and the interior cavity of the main balloon is sealed from the exterior of the main balloon.

In one approach, at least one wire extends through the delivery lumen and out of the at least one hole in the main balloon when then main balloon is in the delivery configuration, and the at least one hole is pre-defined in the wall of the main balloon when the main balloon is in the delivery configuration.

In another approach, at least one wire extends through the delivery lumen and into the interior cavity of the main balloon and terminates within the interior cavity of the balloon when the main balloon is in the delivery configuration.

In one approach, the at least one daughter balloon is outside of the delivery sheath and the balloon catheter when the balloon catheter and delivery sheath are in the delivery configuration.

In another example, a method of supporting or dilating a body vessel includes delivering, to a body vessel, a balloon catheter having a main balloon attached to a shaft where the shaft includes a delivery lumen in fluid communication with an interior cavity of the main balloon, and the main balloon includes at least one hole through an outer wall thereof.

The method further includes delivering at least one daughter balloon through the delivery lumen and into the interior cavity of the main balloon. The daughter balloon is delivered at least partially through the at least one hole in the outer wall of the balloon. The method further includes inflating and expanding the daughter balloon and inflating the main balloon into engagement with a body vessel wall.

The balloon may include at least one pre-loaded wire extending through the delivery lumen and into the interior cavity during delivery of the balloon catheter. The wire may extend through the hole in the balloon either before or after delivering the balloon. The daughter balloon may include a wire lumen, and the daughter balloon is delivered over the wire and into engagement with the hole after delivering the balloon.

The method may further include inflating the daughter balloon into engagement with the hole and sealing the daughter balloon against the hole. The inflation of the main balloon is performed after sealing the hole with the daughter balloon.

The foregoing paragraphs have been provided by way of general introduction, and are not intended to limit the scope of the following claims. The presently preferred embodiments, together with further advantages, will be best understood by reference to the following detailed description taken in conjunction with the accompanying drawings.

BRIEF DESCRIPTION OF SEVERAL VIEWS OF THE DRAWINGS

FIG. 1 shows a balloon catheter having an inflatable balloon having holes formed in an outer wall, and a shaft having a delivery lumen in communication with the interior of the balloon, and wires extending out of the delivery lumen and through the interior of the balloon and out of the holes;

FIG. 2A is a cross-sectional view of one embodiment of the shaft, showing a delivery lumen, an inflation lumen for the balloon, and a wire lumen for delivering the balloon catheter over a guidewire;

FIG. 2B is an alternative embodiment, where the shaft includes a delivery lumen and a guidewire lumen;

FIG. 2C is a schematic cross-sectional view illustrating a tube that extends from the insertion end of the shaft that is integral with the shaft, with the guidewire lumen extending through the tube;

FIG. 3 is a schematic view of a daughter balloon having a shaft and an inflation lumen;

FIG. 4 is a cross-sectional view of the shaft of the daughter balloon;

FIG. 5 is a schematic view of the daughter balloon delivered over the wire through the delivery lumen and into the balloon and out of the hole in the balloon, and inflated into engagement with the hole;

FIG. 5A illustrates a reinforcing band extending around the hole in the balloon;

FIG. 5B illustrates a mesh material embedded in the balloon wall around the hole in the balloon;

FIG. 6 is a view of multiple daughter balloons delivered into the holes of the balloon, and the balloon inflated after each of the daughter balloons have been delivered and inflated;

DETAILED DESCRIPTION

Figure 7:
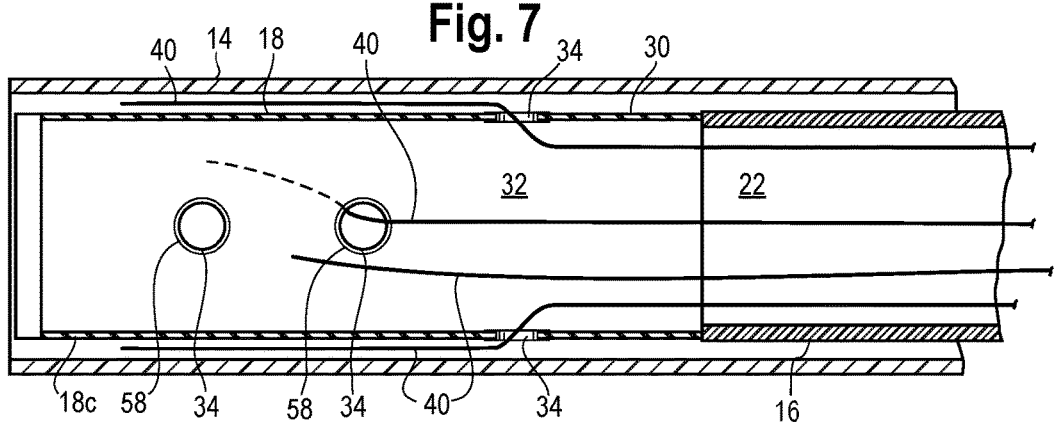
FIG. 7 is a cross-sectional view of the balloon catheter and the balloon in a compressed state within a delivery sheath, with wires preloaded in a delivery state.

Unless defined otherwise, all technical and scientific terms used herein have the same meaning as commonly understood to one of ordinary skill in the art to which this invention belongs.

The term "distal" means a location or direction that is, or a portion of a device that when implanted is further downstream in the direction of or with respect to blood flow. In the case of aortic intervention, distal means a location further away from the heart. In a transfemoral approach, the distal end of a device is the end that is closer to the operator.

The term "proximal" means a location or direction that is, or a portion of a device that when implanted is further upstream in the direction of or with respect to blood flow. In the case of aortic intervention, proximal means a location closer to the heart. In a transfemoral approach, the proximal end of a device is the insertion end of the device.

The term "fenestration" means an opening provided through a surface of a prosthesis from the interior of the prosthesis to the exterior of the prostheses and may have a variety of geometries, including circular, semi-circular, oval, oblong, as well as other geometries.

The term "biocompatible" refers to a material that is substantially non-toxic in the in vivo environment of its intended use, and that is not substantially rejected by the patient's physiological system (i.e., is non-antigenic). Examples of biocompatible materials from which textile graft material can be formed include, without limitation, polyesters, such as polyethylene terephthalate; fluorinated polymers, such as polytetrafluoroethylene (PTFE) and fibers of expanded PTFE, and polyurethanes. In addition, materials that are not inherently biocompatible may be subjected to surface modifications in order to render the materials biocompatible. Examples of surface modifications include graft polymerization of biocompatible polymers on the materials surface, coating of the surface with a crosslinked biocompatible polymer, chemical modification with biocompatible functional groups, and immobilization of a compatibilizing agent such as heparin or other biocompatible substances. Thus, any fibrous material having sufficient strength to survive in the in vivo environment may be used to form a textile graft, provided the final textile is biocompatible. Fibers suitable for making textile grafts include polyethylene, polypropylene, polyaramids, polyacrylonitrile, nylon, and cellulose, in addition to the polyesters, fluorinated polymers, and polyurethanes as listed above. Furthermore, bioremodelable materials may also be used singly or in combination with the aforementioned polymer materials. The textile may be made of one or more polymers that do not require treatment or modification to be biocompatible. The graft may be constructed from woven multifilament polyester, for example and without limitation, Dacron™, produced by DuPONT. Dacron™ is known to be sufficiently biologically inert, non-biodegradable, and durable to permit safe insertion inside the human body.

The term "prosthesis" means any device for insertion or implantation into or replacement for a body part or function of that body part. It may also mean a device that enhances or adds functionality to a physiological system. The term prosthesis may include, for example and without limitation, a stent, stent-graft, filter, valve, balloon, embolization coil, and the like.

The term "tubular" refers to the general shape of an endoluminal device which allows the module to carry fluid along a distance or fit within a tubular structure such as an artery. Tubular prosthetic devices include single, branched, and bifurcated devices. Tubular may refer to any shape including, but not limited to, tapered, cylindrical, curvilinear, or any combination thereof. A tubular device may have a cross-sectional shape that is, circular, substantially circular or the like. However, it should be understood that the cross-sectional shape is not limited thereto, and other shapes, such as, for example, hexagonal, pentagonal, octagonal, or the like are contemplated. The term "endoluminal" refers to or describes objects that can be placed inside a lumen or a body passageway in a human or animal body. A lumen or a body passageway can be an existing lumen or a lumen created by surgical intervention. As used in this specification, the terms "lumen" or "body passageway" are intended to have a broad meaning and encompasses any duct (e.g., natural or iatrogenic) within the human body and can include a member selected from the group comprising: blood vessels, respiratory ducts, gastrointestinal ducts, and the like. "Endoluminal device" or "endoluminal prosthesis" thus describes devices that can be placed inside one of these lumens.

The term "branch vessel" refers to a vessel that branches off from a main vessel. Examples are the celiac and renal arteries which are branch vessels to the aorta (i.e., the main vessel in this context). As another example, the hypogastric artery is a branch vessel to the common iliac, which is a main vessel in this context. Thus, it should be seen that "branch vessel" and "main vessel" are relative terms.

"Longitudinally" refers to a direction, position or length substantially parallel with a longitudinal axis of a reference, and is the length-wise component of the helical orientation.

"Circumferentially" refers to a direction, position, or length that encircles a longitudinal axis of reference. The term "circumferential" is not restricted to a full 360° circumferential turn or to a constant radius.

The terms "patient," "subject," and "recipient" as used in this application refer to any animal, especially humans.

FIGS. 1-10 show a system 10 including a balloon catheter 12 and a delivery sheath 14 for delivering and deploying the balloon catheter 12 within a patient's vasculature at a desired location. As used herein, references to an insertion end refer to the end of a device or component that is inserted first into the patient and that is opposite an operator end, which is the end that typically remains out of the body.

FIG. 1 is a schematic illustration of a balloon 18 in an expanded or partially expanded state that includes holes 34 allowing for additional balloons to pass through at least partially through a wall 30 of the balloon 18. These additional balloons are not shown in FIG. 1 in order to illustrate the holes 34 and other structure. FIG. 1 therefore illustrates the balloon 18 in an expanded condition, but in use, the balloon 18 typically remains in a compressed position prior to the additional balloons being delivered through the holes 34 to seal the holes 34. However, in some approaches, the balloon 18 may be expanded into a partially expanded state to aid in the introduction of the further balloons, as further described below.

The delivery sheath 14 includes an insertion end 14a and an operator end 14b. The balloon catheter 12 likewise includes an insertion end 12a and an operator end 12b.

The balloon catheter 12 includes a main tubular shaft 16 that extends longitudinally between an insertion end 16a and an operator end 16b, and an inflatable balloon 18 attached to the shaft 16 near the insertion end 16a of the shaft 16. As shown in FIG. 1, the insertion end 12a of the overall balloon catheter 12 is disposed further away from the operator than the insertion end 16a of the shaft 16.

The shaft 16 defines an inflation lumen 20 that is in fluid communication with an interior cavity of the balloon 18. In one approach, the inflation lumen 20 may be defined by the shaft 16 and a tube 21 that extends from the insertion end 16a of the shaft 16 and into the interior of the balloon 18 and to the insertion end 12a of the balloon catheter 12. The shaft 16 and the tube 21 may define an inflation port 21a that delivers inflation fluid from the inflation lumen 20 into the interior of the balloon 18, as shown in FIG. 1. In one approach, the tube 21 may be a separate component that attaches to the end of the shaft 16, as illustrated in FIG. 1. Alternatively, as shown in FIG. 2C, the tube 21 may be an integral extension of the shaft 16. In one approach, as shown in FIG. 2C, the tube 21 may provide support for the balloon catheter 12, and may include the guidewire lumen W, but where inflation fluid is provided through another lumen such as a delivery lumen 22, as described below.

The shaft 16 further defines a delivery lumen 22 extending longitudinally through the shaft 16 and configured to allow other system components to be housed therein or delivered therethrough. The catheter 12 and shaft 16 may be delivered with or without the use of a guidewire. In one another approach, the balloon catheter 12 may include a guidewire lumen W formed in the shaft 16 and extending through the tube 21 or other similar support structure that extends through the balloon 18, as shown in FIGS. 1-3. It will be appreciated that the various lumens can be arranged in a variety of ways in the shaft 16 and the through the balloon 18, such that the delivery lumen 22 opens into the interior of the balloon 18 and the inflation lumen 20 can provide inflation fluid to the interior of the balloon, with the guidewire lumen W extending through the balloon 18 and isolated from the inflation lumen 20. One example of a lumen arrangement is shown in FIG. 2A, which shows a cross-section of the shaft 16 and the lumens extending therethrough, including guidewire lumen W, delivery lumen 22 and inflation lumen 20.

FIG. 2B illustrates an embodiment where the shaft 16 includes the delivery lumen 22 and a guidewire lumen W, but without a separate inflation lumen. In this embodiment, inflation fluid may be delivered through the delivery lumen 22. The guidewire lumen W extends through the tube 21 in this embodiment, as shown in FIG. 2C.

In one embodiment, the delivery lumen 22 is sized to be larger/wider than the inflation lumen 20. In particular, the delivery lumen 22 is sized to be wide enough to facilitate delivery of additional balloons through the delivery lumen 22, as well as multiple guidewires for each of the additional balloons, as further described below.

The balloon 18, attached to the insertion end 12a of the catheter 12 as well as to the insertion end 16a of the shaft 16, is preferably in the form of a compliant balloon, meaning that the balloon 18 will typically take the shape of the vessel in which it is deployed once inflated. The balloon 18 is preferably sized to correspond generally to the size of the vessel to which the balloon 18 will be delivered and inflated. The balloon 18 being in the form of a compliant balloon allows the balloon 18 to be inflated to occlude or fill a target blood vessel while limiting instances where the balloon 18 may cause further damage to the vessel wall when inflated. The compliant balloon 18, when inflated, will tend to take the shape of the blood vessel due to its compliant structure. The compliant, or semi-compliant in an alternative approach, balloon 18 helps the balloon 18 accommodate variation in the vascular anatomy that may vary from patient to patient.

In the case of a traditional inflatable balloon, the balloon wall is typically intact such that the balloon will retain the inflation fluid that is introduced into the cavity defined by the balloon to inflate the balloon.

As shown in FIG. 1, the balloon 18 includes the wall 30 that defines an interior cavity 32 therein. The interior cavity 32 is in fluid communication with the inflation lumen 20 of the catheter 12 and the delivery lumen 22 of the shaft 16, such that inflation fluid can be introduced into the interior cavity 32 via the inflation lumen 20 or the delivery lumen 22 to inflate and expand the balloon wall 30 in a manner known in the art, as well as allowing further medical devices to be introduced into the interior cavity 32 via the delivery lumen 22.

Furthermore, the balloon 18 defines one or more holes 34, or punctures or passageways or the like, in the wall 30 that permit the passage of additional structure through the wall 30. Accordingly, with the holes 34 extending through the wall 30, the balloon 18 differs from a traditional balloon in that inflation fluid introduced in a balloon with holes would leak out of the balloon absent other structure that will seal the holes. In the present approach, such structure is provided in the form of additional balloons, which are further described below. In one approach, the balloon wall 30 may include a reinforcing band 58, further described below, that surrounds each of the holes 34 to provide reinforcement to the holes 34 in response to additional balloons being inserted through the holes 34.

In one approach, the holes 34 are generally small. Exemplary holes may be about 2-4 mm in width. The size of the holes 34 are preferably selected to be smaller than the size of the ultimate structure that will be extended through the hole 34, such that after the structure is extended through the hole 34 and left in place, the holes 34 will be generally sealed due to the larger size of the inserted structure exerting a radially outward force on the holes 34, such that the interior cavity 32 within the balloon 18 may still be inflated in response to the introduction of inflation fluid. Accordingly, in one approach, 2-4 mm sized holes are one preferred sizing to accommodate a further balloon that inflates to about 8 mm in width, for example.

In one approach, the balloon 18 may include four holes 34a, 34b, 34c, and 34d. The holes 34a-d are located on the balloon 18 such that their location will typically correspond to the general location of branch vessels in the target delivery and deployment area. For example, the four-hole arrangement may be used in the abdominal aorta near the left and right renal arteries (LRA and RRA) and the supermesenteric artery (SMA) and celiac artery (CA). The SMA and CA are typically disposed above a patient's renal arteries, such that they are between a patient's renal arteries and the heart.

Thus, for a balloon 18 that is designed and arranged to be delivered to this area of the patient, holes 34a and 34b can be arranged on laterally opposite sides of the balloon 18 to accommodate the LRA and RRA, with holes 34c and 34d being disposed longitudinally offset from the holes 34a and 34b and generally on the same lateral side of the balloon 18 as each other. Differing anatomy may result in altering the arrangement of the holes 34 as needed. Further, depending on the desired location for introduction and inflation of the balloon 18, additional holes or fewer holes may be used.

The balloon 18 defines a first end 18a and a second end 18b. The first end 18a is preferably attached to the insertion end 16a of the shaft 16, with the second end 18b being attached to the insertion end 12a of the balloon catheter 12 at the opposite longitudinal end of the balloon 18 opposite the interface between the insertion end 16a of the shaft 16 and the first end 18a of the balloon 18. The delivery lumen 22 includes an opening 22a at the insertion end 16a of the shaft 16 that is in fluid communication with the interior cavity 32 of the balloon, such that wires or other structure can be passed through the delivery lumen 22 and into the interior cavity 32. The delivery lumen 22 therefore could be used for providing inflation fluid as an alternative to the inflation lumen 20 and tube 21, with the tube 21 being used for support rather than inflation, as described above, and the tube 21 may include the guidewire lumen W but remain fluidly isolated from the cavity 32 of the balloon 18, as shown in FIG. 1B.

As shown in FIG. 1, the system 10 may further include one or more wires 40 for assisting in the delivery of additional structure to the holes 34. The wires 40 will act as guidewires for the additional structure to allow for the additional structure to be routed to the desired hole 34. The number of wires 40 preferably corresponds to the number of holes 34 in the balloon 18. However, it will be appreciated that the number of wires 40 could differ from the number of holes 34 in some cases. Typically, each hole 34 will have a corresponding wire 40 extending through the hole 34.

Thus, in one approach, the wires 40 extend through the delivery lumen 22 and out of the insertion end 16a of the shaft 16 and into the interior cavity 32 defined by the balloon 18. Each individual wire 40 may further extend through a corresponding hole 34 of the balloon 18 and out of the interior cavity 32 of the balloon 18, such that a terminal end 42 of the wire 40 is disposed outside of the interior cavity 32. The wires 40 are preferably arranged in a pre-loaded state, such that they extend though the holes 34 of the balloon while the balloon 18 is housed within the delivery sheath 14 prior to insertion into the body. The wires 40 may be preloaded as packaged and provided to the doctor in a pre-loaded state, or the wires 40 may be loaded by the doctor prior to delivery of the catheter 12 into the patient. In either case, the wires 40 are preloaded in the catheter 12 in a delivery configuration prior to insertion into the patient. Thus, by being pre-loaded, the wires 40 may already extend out of the holes 34 and will not need to be routed through the generally small holes 34 of the balloon 18 after the balloon 18 is exposed from the sheath 14 and delivered to the desired delivery area. Accordingly, the wires 40 being pre-loaded will result in the wires 40 extending through the holes 34 prior to the balloon 18 being inflated.

In an alternative approach, the pre-loaded wires 40 may terminate within the balloon cavity 32 when the balloon catheter 12 is delivered in the delivery configuration, and the wires 40 may be carefully routed through the holes 34 after the balloon 18 has been exposed within the body lumen. In this approach, the balloon 18 may be partially inflated to increase the size of the cavity 32 to aid in routing the wires 40. In another approach, the wires 40 may not be pre-loaded and may be introduced through the balloon catheter 12 and into and through the cavity 32 after the balloon 18 has been delivered. FIG. 7 illustrates wires 40 both extending through the holes 34 in the preloaded state and terminating within the cavity 32 in the preloaded state.

Thus, with the wires 40 extending from the delivery lumen 22 through the cavity 32 and out of the balloon 18 to the exterior of the balloon 18, additional components can be delivered along the wires 40 and will be routed to the corresponding hole 34 through which the wires 40 extend.

With reference now to FIGS. 3-6, the system 10 further includes one or more "additional," "secondary," or "daughter" balloons 50 that are configured to be delivered through the delivery lumen 22 over the wires 40 and into engagement with the holes 34 defined by the balloon 18.

FIGS. 3 and 4 shown examples of daughter balloons. The daughter balloons 50 may be attached to a shaft 52 having an inflation lumen 54 and a wire lumen 56 in the manner of a traditional balloon catheter. The inflation lumen 54 provides inflation fluid to the interior of the balloon 50 to inflate and expand the balloon 50 in a manner known in the art, and the balloon 50 and shaft 52 are deliverable over a wire via the wire lumen 56 in a known manner as well. FIG. 4 illustrates one example of a lumen arrangement, showing the shaft 52 in cross-section. However, it will be appreciated that other arrangements of the lumens could be used, such as a dual lumen design for the inflation lumen 54, or a coaxial lumen design where the wire lumen 56 is disposed coaxially within the inflation lumen 54.

Thus, with reference to FIG. 5, in one approach, individual daughter balloons 50 are deliverable over individual wires 40 through the delivery lumen 22 of the shaft 16 and into engagement with the hole 34 that corresponds to the wire 40 over which the particular individual balloon 50 was delivered. FIG. 5 illustrates a first daughter balloon 50 being delivered to one of the holes 34 over the wire 40 that extends through the hole 34. FIG. 5 further illustrates the other holes 34 having wires 40 extending therethrough. FIG. 5 illustrates the balloon 18 in a partially inflated state, however delivery of the daughter balloons 50 may occur when the balloon 18 is still in a compressed state and prior to any inflation. It may be difficult to inflate the balloon 18 effectively prior to delivery of each of the daughter balloons 50 due to the holes 34 being present in the balloon 18.

The daughter balloons 50 may be made from traditional medical balloon materials, and can be compliant or semi-compliant, depending on the needs of the user. The size of the daughter balloons 50 can also be selected to correspond to a patient's particular anatomy. As described above with respect to the holes 34, the expanded width of the balloon 50 is preferably greater than the size of the hole 34, such that when the balloon 50 is expanded into engagement with the hole 34, the edge of the hole 34 will seal against the outer wall of the daughter balloon 50. The compliant nature of the balloon 18 will allow the hole 34 to stretch to accommodate the expanded outer width of the daughter balloon 18. In one approach, the daughter balloons 50 are more rigid than the balloon 18, such that the daughter balloons 50 will stretch the holes 34 in the balloon 18, as shown in FIG. 5. In another approach, the daughter balloons 50 may be less rigid, and in this case the holes 34 may not stretch, and instead the daughter balloons 50 would expand further on each side of the hole 34 than in the hole 34, such that the diameter of the daughter balloon 50 on either side of the hole 34 is greater than the diameter of the hole 34, thus taking on a somewhat hourglass shape, as shown in FIG. 6.

The balloons 50 are preferably delivered over the wires 40 in a sequential manner, such that the delivery lumen 22 of the shaft 16 can be sized to accommodate the number of preloaded wires 40 in addition to allowing a single balloon 50 to be delivered through the lumen 22, which keeps the overall width of the shaft 16 small. However, it would also be possible to increase the size of the delivery lumen 22 to allow for delivery of more than one balloon 50 at a time side-by-side, but this would also increase the width of the shaft 16 to a size larger than one where balloons 50 are delivered sequentially.

FIG. 6 illustrates the balloon 18 in a fully inflated state after each of the daughter balloons 50 have been delivered to the corresponding holes 34 over the corresponding wires 40. The balloons 50 have been inflated and have created a seal with the holes 34, thereby sealing off the cavity 32 inside the balloon 18 such that the balloon 18 may be inflated. FIG. 6 illustrates the example of the daughter balloons 50 taking on an hourglass shape after inflation, as described above.

Due to the expansion of the balloons 50 while extending through the holes 34 to create the seal, the balloon 34 may also include the reinforcing band 58 disposed around the edge of the holes 34, as shown in FIG. 5A. The reinforcing band 58 can help prevent tearing of the balloon 18 at the location of the holes 34 when the holes 34 are stretched, and can also help provide a seal against the expanded daughter balloon 50. As shown in FIG. 5A, the reinforcing band 58 can be in the form of an additional layer of balloon material that is bonded or adhered to the area surrounding the hole, or it could be in the form of an applied coating or curing adhesive. In another approach, as shown in FIG. 5B, a mesh material 59 may be embedded in the wall 30 of the balloon 18 around the holes 34.

When the daughter balloons 50 are expanded into a sealing engagement with the holes 34 of the balloon 18, the balloon 18 will be generally sealed from inflation fluid leaking out of the balloon 18 when the balloon 18 is inflated. It has been found that the use of 8×20 mm sized daughter balloons 50 inserted into 2-4 mm holes 34 in the balloon 18 allows the balloon 18 to hold greater than 1 atm of pressure when inflation fluid is introduced into the cavity 32 to inflate the balloon 32. As shown in FIG. 5, the balloon 18 and the holes 34 thereof, the daughter balloons 50, and shaft 16, as well as other structure described above, can each include radiopaque markers 61 disposed at various selected locations to aid in locating the balloon 18 and the various corresponding and cooperating structure at the desired location within the patient's anatomy. For example, markers 61 may be located at each of the holes 34 to assist in positioning the balloon 18 so that the wires 40 and daughter balloons 50 may be routed to the desired branch vessels. Similarly, the wires 40 may be made of a radiopaque material.

The daughter balloons 50 can be used to cannulate various branch vessels adjacent the delivered location of the main balloon 18. This can be performed quickly and easily due to the pre-loaded wires 40 that extend through the balloon 18 in its delivery state. The wires 40 are moveable relative to the shaft 16 and the holes 34 of the balloon 18, such that after the balloon 18 and wires 40 have been delivered, the wires 40 can be individually extended into the desired branch vessel prior to delivering the daughter balloon 50. Accordingly, the daughter balloon 50 will enter the desired branch vessel along the wire 40.

The system 10 has a delivery state and a deployed state. With reference to FIG. 7, in the delivery state, the balloon 18 and shaft 16 and wires 40 are disposed within the delivery sheath 14 and covered by the delivery sheath 14. The wires 40 are pre-loaded in the balloon 18. FIG. 7 shows three wires 40 extending through the holes 34 in the balloon 34 such that they extend through the holes 34 and to the exterior of the balloon 18 while in the delivery state. FIG. 7 also illustrates one wire 40 terminating within the balloon cavity 32. It will be appreciated that all of the wires 40 may extend out of the holes 34 in the delivery state, all of the wires 40 may terminate with the cavity 32 in the delivery state, or some of the wires 40 may extend out of the holes 34 and others of the wires 40 may terminate within the balloon cavity 32.

Figure 8:
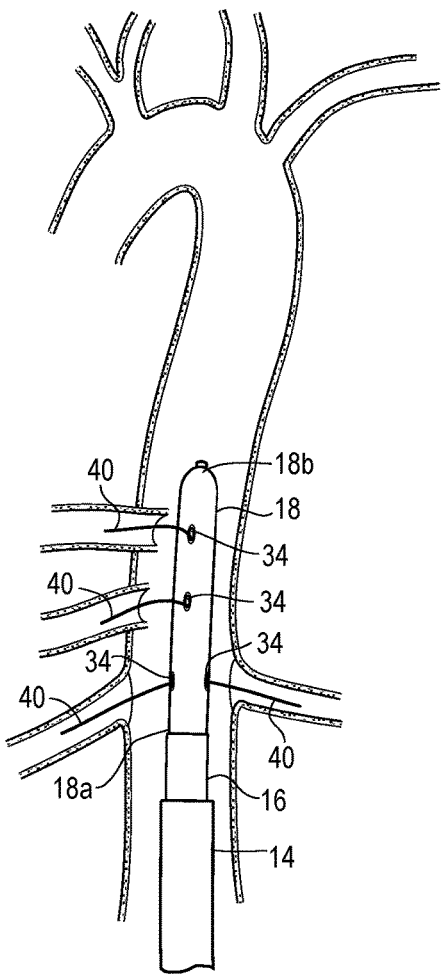
FIG. 8 illustrates the balloon catheter delivered to a body vessel and exposed from the delivery sheath, with the wires being routed into adjacent branch vessels from the holes in the balloon.

In the deployed state, shown in FIG. 8, the delivery sheath 14 is retracted relative to the balloon 18, shaft 16, and wires 40, thereby exposing the balloon 18 and the wires 14 to the surrounding vasculature. From this deployed state, the wires 40 may be routed into the desired branch vessels, and the balloons 50 may be introduced as described above and the balloon 18 may be inflated.

Figure 9:
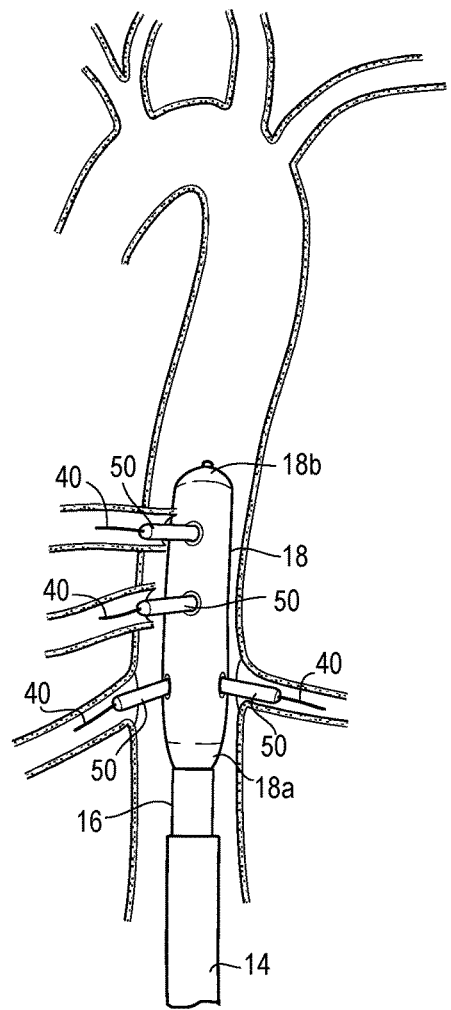
FIG. 9 illustrates the daughter balloons delivered across the holes and inflated into engagement with the holes and extending into the branch vessels.

As shown in FIG. 8, upon the balloon 18 being exposed by retracting the sheath 14 at the desired location, the wires 40 are routed into the desired adjacent branch vessels. As shown in FIG. 9, following positioning of the wires 40, the daughter balloons 50 are delivered over the wires 40 and into the branch vessels while also being disposed within the holes 34 of the balloon 18. The balloons 50 are preferably delivered sequentially. However, as described above, in another approach multiple balloons 50 may be delivered side-by-side or otherwise together if the delivery lumen 22 is wide enough to accommodate multiple daughter balloons 50 in that arrangement.

After delivering the daughter balloons 50 over the wires 40 and into the holes 34 of the balloon 18, the daughter balloons 50 are inflated. The daughter balloons 50 can be inflated sequentially after delivering each individual balloon 50, or multiple balloons 50 may be inflated at the same time after delivering multiple balloons 50. In another approach, the balloons 50 could each be inflated at the same time after some or all of the balloons 50 have been delivered.

As the balloons 50 are inflated, they can be inflated to provide support to the branch vessels. In another approach, the balloons 50 may be positioned at different areas outside of the balloon 18 outside of a branch vessel. For example, one or more of the balloons 50 could be positioned against the main vessel wall.

Figure 10:
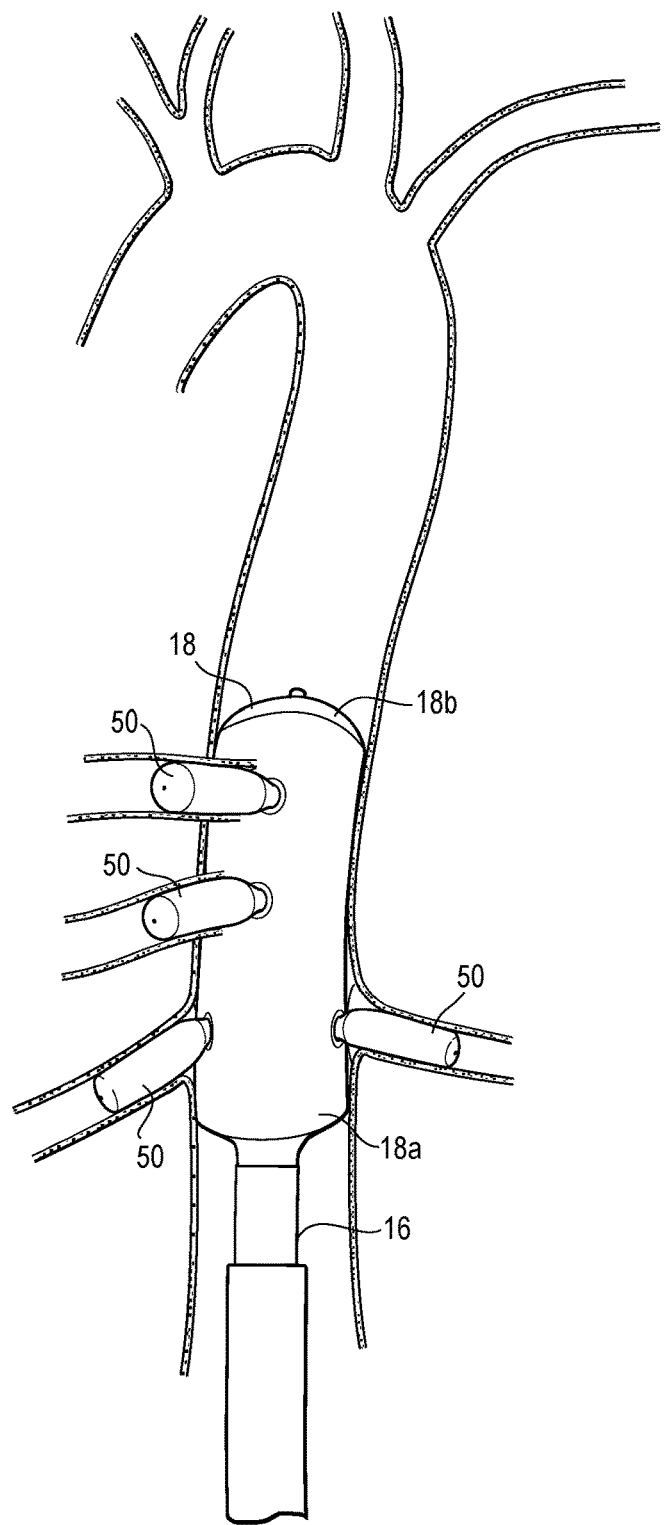
FIG. 10 illustrates the balloon in an inflated condition and expanded into contact with the body vessel wall with the daughter balloons inflated into engagement with the branch vessels.

As shown in FIG. 10, after each of the daughter balloons 50 have been inflated, the main balloon 18 is inflated and expanded into engagement with the main vessel wall. The previous inflation of the daughter balloons 50 provides a sealing and filling of the holes 34, such that the main balloon 18 will sufficiently inflate.

In one approach, the balloon 18 is compliant, and the daughter balloons 50 are minimally compliant, meaning that the daughter balloons 50 can inflate to a predefined shape, causing the balloon 18 to stretch in response to inflation of the daughter balloons 50. Therefore, when the balloon 18 is inflated, it will tend to conform to the shape of the vessel wall as well as around the daughter balloons 50. In another approach, the daughter balloons 18 may be compliant and will take the shape of the vessel in which they are deployed, and inflation of the balloon 18 may alter the shape of the daughter balloons 50, depending on whether the balloon 18 or daughter balloons 50 are more rigid relative to each other.

The main balloon 18 can be cycled between an inflated and deflated position to open up a blocked blood vessel. In this case, the daughter balloons 50 provide support to the branch vessels as the main balloon 18 is inflated and deflated. While the balloon 18 has been described as being compliant and conforming to the shape of the vessel, it will be appreciated that the balloon 18 may still be arranged to have sufficient rigidity when inflated to open up a blocked vessel.

In the case of aortic dissection, such as type B dissection, the daughter balloons 50 in their inflated state provide support to the branch vessels, while the inflation of the main balloon 18 provides support within the true lumen, thereby allowing for filling the false lumen with embolic material.

It will be appreciated that the above arrangement may be used in various other situations where balloon support for a main vessel and branch vessels is desired.

Throughout this specification various indications have been given as to preferred and alternative examples and aspects of the invention. However, the foregoing detailed description is to be regarded as illustrative rather than limiting and the invention is not limited to any one of the provided aspects. It should be understood that it is the appended claims, including all equivalents that are intended to define the spirit and scope of this invention.

I claim:

1. A medical device system comprising:
   a balloon catheter including a shaft extending in a longitudinal direction and an inflatable main balloon attached to the catheter;
   an inflation lumen defined by the shaft and extending longitudinally within the shaft, the inflation lumen in fluid communication with an interior cavity defined by the balloon for providing inflation fluid to the main balloon;

a delivery lumen defined by the shaft and extending longitudinally through the shaft, the delivery lumen in fluid communication with the interior cavity of the balloon and configured to allow additional medical devices to be delivered to the interior cavity of the main balloon;

at least one inflatable daughter balloon sized and configured to be moveable through the delivery lumen and into the interior cavity of the main balloon; and at least one hole defined in an expandable wall portion of the main balloon, the at least one hole sized and configured to receive individual ones of the at least one daughter balloon;

wherein the at least one daughter balloon is expandable into engagement with the at least one hole.

2. The system of claim 1, wherein the inflatable main balloon is a compliant balloon.

3. The system of claim 2, wherein the daughter balloon is a minimally compliant balloon.

4. The system of claim 1, wherein the at least one hole is pre-defined in the wall of the main balloon.

5. The system of claim 1 further comprising at least one wire extending through the delivery lumen and into the interior cavity of the main balloon from the delivery lumen.

6. The system of claim 5, wherein the at least one wire is preloaded in the system and extends through the at least one hole when preloaded.

7. The system of claim 5, wherein the daughter balloon includes a wire lumen and is delivered over the wire into engagement with the hole.

8. The system of claim 1, wherein the delivery lumen has a tubular shape and is wider than the inflation lumen.

9. The system of claim 1, wherein the at least one daughter balloon sealingly engages the at least one hole when the at least one daughter balloon is expanded such that the main balloon is expandable via inflation after the at least one daughter balloon is inflated.

10. The system of claim 9, wherein the at least one hole stretches in response to inflation of the daughter balloon.

11. The system of claim 1, wherein the at least one daughter balloon has an expanded width that is smaller than an expanded width of the main balloon.

12. The system of claim 1, wherein the main balloon is reinforced in an area around the at least one hole.

13. A medical device system comprising:

a balloon catheter including a shaft extending in a longitudinal direction and an inflatable main balloon attached to the catheter, the main balloon defining an interior cavity;

a delivery lumen defined by the shaft and extending longitudinally through the shaft, the delivery lumen in fluid communication with the interior cavity of the balloon and configured to allow additional medical devices to be delivered to the interior cavity of the main balloon;

at least one inflatable daughter balloon sized and configured to be moveable through the delivery lumen and into the interior cavity of the main balloon;

at least one hole defined in an expandable wall portion of the main balloon, the at least one hole sized and configured to receive individual ones of the at least one daughter balloon; and a tubular delivery sheath extending over the balloon catheter, wherein the balloon catheter has a delivery configuration where the balloon catheter is in a retracted position relative to an insertion end of the delivery sheath and the balloon catheter compressed within the delivery sheath, and the balloon catheter has a deployed configuration where the insertion end of the delivery sheath is retracted relative to the balloon catheter to expose the balloon catheter;

wherein, in the delivery configuration, the interior cavity of the main balloon is in fluid communication with an exterior of the main balloon via the at least one hole, and the at least one daughter balloons is not engaged with the at least one hole; and wherein, in the deployed configuration, the at least one daughter balloon is engaged with the at least one hole of the main balloon and the at least one daughter balloon is inflated against the at least one hole and the interior cavity of the main balloon is sealed from the exterior of the main balloon.

14. The system of claim 13, further comprising at least one wire extending through the delivery lumen and out of the at least one hole in the main balloon when the main balloon is in the delivery configuration, wherein the at least one hole is pre-defined in the wall of the main balloon when the main balloon is in the delivery configuration.

15. The system of claim 13, further comprising at least one wire extending through the delivery lumen and into the interior cavity of the main balloon and terminating within the interior cavity of the balloon when the main balloon is in the delivery configuration.

16. The system of claim 13, wherein the at least one daughter balloon is outside of the delivery sheath and the balloon catheter when the balloon catheter and delivery sheath are in the delivery configuration.

* * * * *